United States Patent
Rao et al.

(10) Patent No.: US 6,361,996 B1
(45) Date of Patent: *Mar. 26, 2002

(54) NEUROEPITHELIAL STEM CELLS AND GLIAL-RESTRICTED INTERMEDIATE PRECURSORS

(75) Inventors: Mahendra S. Rao, Salt Lake City; Margot Mayer-Proschel, Sandy, both of UT (US)

(73) Assignee: University of Utah Research Foundation, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/852,744

(22) Filed: May 7, 1997

(51) Int. Cl.[7] .................................................. C12N 5/06
(52) U.S. Cl. ...................................... 435/353; 435/325
(58) Field of Search ................................ 435/325, 368, 435/353

(56) References Cited

U.S. PATENT DOCUMENTS

| | | | | |
|---|---|---|---|---|
| 5,411,883 A | * | 5/1995 | Boss et al. ................ | 435/240.2 |
| 5,589,376 A | | 12/1996 | Anderson et al. ......... | 435/240.2 |
| 5,753,506 A | * | 5/1998 | Johe et al. ................... | 435/377 |

OTHER PUBLICATIONS

Cattarreo et al. Nature 347: 762–765, 1990.*
Gage, F.H., et al, Isolation, Characterization and Use of Stem Cells from the CNS, 18 Ann. Rev. Neurosci. 159–92 (1995).
Marvin, M., et al, Multipotential Stem Cells in the Vertebrate CNS, 3 Semin. Cell. Biol. 401–11 (1992).
Davis, A.A., et al, A Self–Renewing Multipotential Stem Cell in Embryonic Rat Cerebral Cortex, 362 Nature 363–72 (1994).
Gritti, A.G., et al, Multipotential Stem Cells from the Adult Mouse Brain Proliferate and Self–Renew in Response to Basic Fibroblast Growth Factor, 16 J. Neurosci. 1091–1100 (1996).
Reynolds, B.A., et al, A Multipotent EGF–Responsive Striatal Embryonic Progenitor Cell Produces Neurons and Astrocytes, 12 J. Neurosci. 4565–74 (1992).
Reynolds, B.A., et al, Clonal and Population Analyses Demonstrate that an EGF–Responsive Mammalian Embryonic CNS Precursor is a Stem Cell, 175 Development Biol. 1–13 (1996).
Williams, B.P., The Generation of Neurons and Oligodendrocytes from a Common Precursor Cell, 7 Neuron 685–93 (1991).
Kilpatrick, T.J., et al, Cloned Multipotential Precursors from the Mouse Cerebrum Require FGF–2, Whereas Glial Restricted Precursors are Stimulated with Either EGF–2 or EGF, 15 J. Neurosci. 3653–61 (1995).
Price, J., et al, Lineage Analysis in the Vertebrate Nervous System by Retrovirus–Mediated Gene Transfer, 84 Developmental Biol. 156–60 (1987).
Williams, B., Precursor Cell Types in the Germinal Zone of the Cerebral Cortex, 17 BioEssays 391–93 (1995).
Hamburger, V., The Mitotic Patterns in the Spinal Cord of the Chick Embryo and Their Relation to the Histogenic Process, 88J. Comp. Neurol. 221–84 (1948).
Nornes, H.O., et al, Temporal Pattern of Neurogenesis in the Spinal Cord of Rat. 1. An Autoradiographic Study—Time and Sites of Origin and Migration and Settling Patterns of Neuroblasts, 73 Brain Res. 121–38 (1974).
Altman, J., et al, The Development of the Rat Spinal Cord, 85 Adv. Anat. Embryol. Cell Biol. 32–46 (1984).
Phelps, P.E., et al, Generation Patterns of Four Groups of Cholinergic Neurons in Rat Cervical Spinal Cord: A Combined Tritiated Thymidine Autoradiographic and Choline Acetyltransferase Immunocytochemical Study, 273 J. Comp. Neurol. 459–72 (1988).
Phelps, P.E., et al, Embryonic Development of Four Different Subsets of Cholinergic Neurons in Rat Cervical Spinal Cord, 291 J. Comp. Neurol. 9–26 (1990).
Chen, E.W., et al, Early Stages in the Development of Spinal Motor Neurons, 320 J. Comp. Neurol. 291–303 (1992).
Dodd, J., et al, Spatial Regulation of Axonal Glycoprotein Expression on Subsets of Embryonic Spinal Neurons, 1 Neuron 105–16 (1988).
Erickson, J., et al, Early Stages of Motor Neuron Differentiation Revealed by Expression of Homebox Gene Islet–1, 256 Science 1555–59 (1992).
Hirano, M., et al, Gliogenesis in the Rat Spinal Cord: Evidence for Origin of Astrocytes and Oligodendrocytes from Radial Precursors, 21 J. Neurosci. Res. 155–67 (1988).
Warf, B.C., Evidence for the Ventral Origin of Oligodendrocyte Precursors in the Rat Spinal Cord, 11 J. Neurosci. 2477–88 (1991).
Pringle, N.P., et al, A Singularity of PDGF Alpha–Receptor Expression in the Dorsoventral Axis of the Neural Tube May Define the Origin of the Oligodendrocyte Lineage, 117 Developments 525–33 (1993).

(List continued on next page.)

Primary Examiner—Gary L. Kuntz
Assistant Examiner—Robert C. Hayes
(74) Attorney, Agent, or Firm—Licata & Tyrrell P.C.

(57) ABSTRACT

Multipotent neuroepithelial stem cells and lineage-restricted oligodendrocyte-astrocyte precursor cells are described. The neuroepithelial stem cells are capable of self-renewal and of differentiation into neurons, astrocytes, and oligodendrocytes. The oligodendrocyte-astrocyte precursor cells are derived from neuroepithelial stem cells, are capable of self-renewal, and can differentiate into oligodendrocytes and astrocytes, but not neurons. Methods of generating, isolating, and culturing such neuroepithelial stem cells and oligodendrocyte-astrocyte precursor cells are also disclosed.

19 Claims, 2 Drawing Sheets

OTHER PUBLICATIONS

Anderson, D.J., The Neural Crest Cell Lineage Problem: Neuropoiesis? 3 Neuron 1–12 (1989).

Ray, J., et al, Spinal Cord Neuroblasts Proliferate in Response to Basic Fibroblast Growth Facto, 14 J. Neurosci. 3548–64 (1994).

Bronner–Fraser, M., et al., Cell Lineage Analysis Slows Multipotency of Some Avian Neural Crest Cells, 355 Nature 161–64 (1988).

Murphy, M., et al, Fibroblast Growth Factor Stimulates the Proliferation and Differentiation of Neural Precursor Cell In Vitro, 25 J. Neurosci. Res. 463–75 (1990).

Drago, J., et al, Fibroblast Growth Factor–Mediated Proliferation of Central Nervous System Precursors Depends on Endogenous Production of Insulin–like Growth Factor 1, 88 Proc. Nat'l Acad. Scie. USA 2199–2203 (1991).

Kilpatrick, T.J., et al, Cloning and Growth of Multipotential Neural Precursors: Requirements for Proliferation and Differentiation, 10 Neuron 255–65 (1993).

Bannerman, P.G., et al, Protein Growth Factor Requirements of Rat Neural Crest Cells, 36 J. Neurosci. Res. 46–57 (1993).

Stemple, D.L., et al, Isolation of a Stem Cell for Neurons and Glia from the Mammalian Neural Crest, 71 Cell 973–85 (1992).

Sommers, L, et al, The Cellular Function of MASH1 in Automonic Neurogenesis, 15 Neuron 1245–58 (1995).

Lendahl, U., et al, CNS Stem Cells Express a New Class of Intermediate Filament Protein, 60 Cell 585–95 (1990).

Camu, W., et al, Purification of Embryonic Rat Motoneurons by Panning on a Monoclonal Antibody to the Low–affinity NGF Receptor, 44 J. Neurosci. Meth. 59–70 (1992).

Raff, M., Glial Cell Diversification in the Rat Optic Nerve, 243 Science 1450–55 (1989).

Lillien, L.E., et al, Analysis of the Cell–Cell Interactions that Control Type–2 Astrocyte Development In Vitro, 4 Neuron 525–34 (1990).

Vescovi, A.L., et al, bFGF Regulates the Proliferative Fate of Unipotent (Neuronal) and Bipotent (Neuronal/Astroglial) EGF–Generated CNS Progenitor Cells, 11 Neuron 951–66 (1993).

Temple, S., et al, Isolated Rat Cortical Progenitor Cells are Maintained in Division In Vitro by Membrane–Associated Factors, 120 Development 999–1008 (1994).

Aloisi, F., et al, Developmental Appearance, Antigenic Profile, and Proliferation of Glial Cells of the Human Embryonic Spinal Cord: An Immunocytochemical Study Using Dissociated Cultured Cells, 5 Glial 181 (1992).

Cameron, R.S., et al., Glial Cell Lineage in Cerebral Cortex: A Review and Synthesis, 5 Glia 124–37 (1991).

Chan, C.L., et al, Oligodendrocyte–type 1 Astrocyte (O–2A) Progenitor Cells from Neonatal and Adult Rat Optic Nerve Differ in Their Responsiveness to Platelet–Derived Growth Factor, 55 Brain Res. Dev. Brain Res. 275–82 (1990).

Elder, G.A., et al, Characterization of Glial Subpopulations in Cultures of the Ovine Central Nervous System, 1 Glia 317–27 (1988).

Fok–Seang, J., et al, Distribution and Differentiation of A2B5+ Glial Precursors in the Developing Rat Spinal Cord, 37 J Neurosci. Res. 219–35 (1994).

Fulton, B.P., et al, Visualization of O–2A Progenitor Cells in Developing an Adult Rat Optic Nerve by Quisqualate–Stimulated Cobalt Uptake, 12 J. Neurosci. 4816–33 (1992).

Galileo, D.S., et al, Neurons and Glia Arise from a Common Progenitor in Chicken Optic Tectum: Demonstration with Two Retroviruses and Cell Type–Specific Antibodies, 87 Proc. Nat'l Acad. Sci. USA 458–62 (1990).

Gard, A.L., et al, Oligodendroblasts Distinguished from O–2A Glial Progenitors by Surface Phenotype (O4+GalC–) and Response to Cytokines Using Signal Transducer LIFR $\beta$, 167Dev. Biol. 596–608 (1995).

Hardy, R., et al, Proliferation and Differentiation Potential of Rat Forebrain Oligodendroglial Progenitors Both In Vitro and In Vivo, 111 Development 1061–80 (1991).

Hardy, R.J., et al., Oligodendrocyte Progenitors Are Generated Throughout the Embryonic Mouse Brain, But Differentiate in Restricted Foci, 122 Development 2059–69 (1996).

Knapp, P.E., Studies of Glial Lineage and Proliferation In Vitro Using an Early Marker for Committed Oligodendrocytes, 30 J. Neuerosci. Res. 336–45 (1991).

Luskin, M.B., et al, Neurons, Astrocytes, and Oligodendrocytes of the Rat Cerebral Cortex Originate from Separate Progenitor Cells: An Ultrastructural Analsysis of Clonally Related Cells, 13 J. Neurosci. 1730–50 (1993).

Miller, R.H., Oligodendrocyte Origins, 19 TINS 92–96 (1996).

Ono, K., et al, Early Development and Dispersal of Oligodendrocyte Precursors in the Embryonic Chick Spinal Cord, 121 Development 1743–54 (1995).

Raff, M.C., et al, A Glial Progenitor Cell That Develops In Vitro into an Astrocyte or an Oligodendrocyte Depending on Culture Medium, 303 Nature 390–96 (1983).

Rivkin, M.J., et al, Oligodendroglial Development in Human Fetal Cerebrum, 38 Ann. Neurol. 92–101 (1995).

Eisenbarth, G.S., et al, Monoclonal Antibody to Plasma Membrane Antigen of Neurons, 76 Proc. Nat'l Acad. Sci. USA 4913–17 (1979).

Geisert, E.E., et al, The Neuronal Response to Injury As Visualized by Immunostaining of Class $\beta$–tubulin in the Rat, 102 Neurosci. Lett. 137–41 (1989).

Sommer, I., et al, Monoclonal Antibodies (O1–O4) to Oligodendrocyte Cell Surfaces: An Immunocytological Study in the Central Nervous System, 83 Dev. Biol. 311–27 (1981).

Trimmer, P.A., et al, Combination of In Situ Hybridization and Immunocytochemistry to Detect Messenger RNAs in Identified CNS Neurons and Glia in Tissue Culture, 39 J. Histochem. Cytochem. 891–8 (1991).

Wysocki, L.J., et al, "Panning" for Lymphocytes: A Method for Cell Selection, 75 Proc. Nat'l Acad. Sci. 2844–48 (1978).

Mayer, M., et al, Ciliary Neurotrophic Factor and Leukemia Inhibitory Factor Promote the Generation, Maturation, and Survival of Oligodendrocytes, 120 Development 142–53 (1994).

Bottenstein, J.E., et al, Growth of Rat Neuroblastoma Cell Line in Serum–Free Supplemented Medium, 76 Proc. Nat'l Acad. Sci. USA 514–17 (1979).

Lillien, L.E., et al, Differentiation Signals in the CNS: Type–2 Astrocyte Development In Vitro as a Model System, 5 Neuron 5896–6273 (1990).

* cited by examiner

NEUROEPITHELIAL STEM CELLS AND GLIAL-RESTRICTED INTERMEDIATE PRECURSORS

BACKGROUND OF THE INVENTION

This invention relates to multipotent neuroepithelial stem cells, lineage-restricted intermediate precursor cells, and methods of making thereof. More particularly, the invention relates to neuroepithelial stem cells that retain the capabilities of self-renewal and differentiation into neurons, astrocytes, and oligodendrocytes. Further, the invention relates to oligodendrocyte-astrocyte-restricted precursor cells that are capable of self-renewal and differentiation into astrocytes and oligodendrocytes, but not neurons. Methods of generating, isolating, and culturing such neuroepithelial stem cells and oligodendrocyte-astrocyte precursor cells are also described.

Multipotent cells with the characteristics of stem cells have been identified in several regions of the central nervous system and at several developmental stages. F. H. Gage et al., Isolation, Characterization and Use of Stem Cells from the CNS, 18 Ann. Rev. Neurosci. 159–92 (1995); M. Marvin & R. McKay, Multipotential Stem Cells in the Vertebrate CNS, 3 Semin. Cell. Biol. 401–11 (1992); R. P. Skoff, The Lineages of Neuroglial Cells, 2 The Neuroscientist 335–44 (1996). These cells, often referred to as neuroepithelial stem cells (NEP cells), have the capacity to undergo self renewal and to differentiate into neurons, oligodendrocytes, and astrocytes, thus representing multipotent stem cells. A. A. Davis & S. Temple, A Self-Renewing Multipotential Stem Cell in Embryonic Rat Cerebral Cortex, 362 Nature 363–72 (1994); A. G. Gritti et al., Multipotential Stem Cells from the Adult Mouse Brain Proliferate and Self-Renew in Response to Basic Fibroblast Growth Factor, 16 J. Neurosci. 1091–1100 (1996); B. A. Reynolds et al., A Multipotent EGF-Responsive Striatal Embryonic Progenitor Cell Produces Neurons and Astrocytes, 12 J. Neurosci. 4565–74 (1992); B. A. Reynolds & S. Weiss, Clonal and Population Analyses Demonstrate that an EGF-Responsive Mammalian Embryonic CNS Precursor is a Stem Cell, 175 Developmental Biol. 1–13 (1996); B. P. Williams et al., The Generation of Neurons and Oligodendrocytes from a Common Precursor Cell, 7 Neuron 685–93 (1991).

The nervous system also contains precursor cells with restricted differentiation potentials. T. J. Kilpatrick & P. F. Bartlett, Cloned Multipotential Precursors from the Mouse Cerebrum Require FGF-2, Whereas Glial Restricted Precursors are Stimulated with Either FGF-2 or EGF, 15 J. Neurosci. 3653–61 (1995); J. Price et al., Lineage Analysis in the Vertebrate Nervous System by Retrovirus-Mediated Gene Transfer, 84 Developmental Biol. 156–60 (1987); B. A. Reynolds et al., supra; B. A. Reynolds & S. Weiss, supra; B. Williams, Precursor Cell Types in the Germinal Zone of the Cerebral Cortex, 17 BioEssays 391–93 (1995); B. P. Williams et al., supra. The relationship between multipotent stem cells and lineage restricted precursor cells is still unclear. In principal, lineage restricted cells could be derived from multipotent cells, but this is still a hypothetical possibility in the nervous system with no direct experimental evidence.

During development, the neuroepithelial cells that comprise the caudal neural tube differentiate into neurons and glia. Neurons arise from neuroepithelial precursors first and eventually develop unique phenotypes defined by their trophic requirements, morphology, and function. Motoneurons are among the first neurons to develop. V. Hamburger, The Mitotic Patterns in the Spinal Cord of the Chick Embryo and Their Relationship to the Histogenic Process, 88 J. Comp. Neurol. 221–84 (1948); H. O. Nornes & G. D. Das, Temporal Pattern of Neurogenesis in the Spinal Cord of Rat. 1. Time and Sites of Origin and Migration and Settling Patterns of Neuroblasts, 73 Brain Res. 121–38 (1974); J. Altman & S. Bayer, The Development of the Rat Spinal Cord, 85 Adv. Anat. Embryol. Cell Biol. 32–46 (1984); P. E. Phelps et al., Generation Patterns of Four Groups of Cholinergic Neurons in Rat Cervical Spinal Cord: A Combined Tritiated Thymidine Autoradiographic and Choline Acetyltransferase Immunocytochemical Study, 273 J. Comp. Neurol. 459–72 (1988); P. E. Phelps et al., Embryonic Development of Four Subsets of Cholinergic Neurons in Rat Cervical Spinal Cord, 291 J. Comp. Neurol. 9–26 (1990). Motoneurons can be distinguished from other neurons present in the spinal cord by their position and the expression of a number of specific antigens. E. W. Chen & A. Y. Chiu, Early Stages in the Development of Spinal Motor Neurons, 320 J. Comp. Neurol. 291–303 (1992). Tag-1, J. Dodd et al., Spatial Regulation of Axonal Glycoprotein Expression on Subsets of Embryonic Spinal Neurons, 1 Neuron 105–16 (1988), islet-1, J. Erickson et al., Early Stages of Motor Neuron Differentiation Revealed by Expression of Homeobox Gene Islet-1, 256 Science 1555–59 (1992), and p75, W. Camu & C. E. Henderson, Purification of Embryonic Rat Motorneurons by Panning on a Monoclonal Antibody to the Low-Affinity NGF Receptor, 44 J. Neurosci. 59–70 (1992), are expressed uniquely on rat and chick motoneurons early in their development, but are not detectable on other spinal cord cells and, therefore, may serve to distinguish motoneurons from other neural tube cells. Astrocytes, characterized by glial fibrillary acidic protein (GFAP) immunoreactivity, appear soon after; GFAP staining is seen at embryonic day 16 (E16). M. Hirano & J. E. Goldman, Gliogenesis in the Rat Spinal Cord: Evidence for the Origin of Astrocytes and Oligodendrocytes from Radial Precursors, 21 J. Neurosci. Res. 155–67 (1988). Astrocytic cells proliferate and populate the gray and white matter of the spinal cord, and both type 1 and type 2 astrocytes have been identified in the spinal cord. B. C. Warf et al., Evidence for the Ventral Origin of Oligodendrocytic Precursors in the Rat Spinal Cord, 11 J. Neurosci. 2477–88 (1991). Oligodendrocytes appear later and are first detected around birth, though oligodendrocyte precursors may be present as early as E14 based on platelet derived growth factor alpha-receptor (PDGFRA) expression and culture assays. N. P. Pringle & W. D. Richardson, A Singularity of PDGF Alpha-Receptor Expression in the Dorsoventral Axis of the Neural Tube May Define the Origin of the Oligodendrocyte Lineage, 117 Development 525–33 (1993); B. C. Warf et al., supra.

As will be shown herein, NEP cells grow on fibronectin and require fibroblast growth factor (FGF) and an as yet uncharacterized component present in chick embryo extract (CEE) to proliferate and maintain an undifferentiated phenotype in culture. The growth requirements of NEP cells are different from neurospheres isolated from E14.5 cortical ventricular zone cells. B. A. Reynolds et al., supra; B. A. Reynolds & S. Weiss, supra; WO 9615226; WO 9615224; WO 9609543; WO 9513364; WO 9416718; WO 9410292; WO 9409119. Neurospheres grow in suspension culture and do not require CEE or FGF, but are dependent on epidermal growth factor (EGF) for survival. FGF itself is not sufficient for long term growth of neurospheres, though FGF may support their growth transiently. The presently described NEP cells grow in adherent culture, are FGF dependent, do not express detectable levels of EGF receptors, and are isolated at a stage of embryonic development prior to which it has been possible to isolate neurospheres. Thus, NEP cells may represent a multipotent precursor characteristic of the brain stem and spinal cord, while neurospheres may represent a stem cell more characteristic of the cortex.

U.S. Pat. No. 5,589,376, to D. J. Anderson and D. L. Stemple, discloses mammalian neural crest stem cells and methods of isolation and clonal propagation thereof, but fails to disclose cultured NEP cells, cultured lineage restricted precursor cells, and methods of generating, isolating, and culturing thereof. Neural crest cells differentiate into neurons and glia of the peripheral nervous system (PNS), whereas the present neuroepithelial stem cells differentiate into neurons and glia of the central nervous system (CNS).

The present invention is necessary to understand how multipotent neuroepithelial stem cells become restricted to the various neuroepithelial derivatives. In particular, culture conditions that allow the growth and self-renewal of mammalian neuroepithelial stem cells are desirable so that the particulars of the development of these mammalian stem cells can be ascertained. This is desirable because a number of tumors of neuroepithelial derivatives exist in mammals, particularly humans. Knowledge of mammalian neuroepithelial stem cell development is therefore needed to understand these disorders in humans. Additionally, the ability to isolate and grow mammalian neuroepithelial stem cells in vitro allows for the possibility of using such stem cells to treat neurological disorders in mammals, particularly humans. Further, such mammalian neuroepithelial stem cells can be used therapeutically for treatment of certain diseases, e.g. Parkinson's Disease, such as by transplantation of such cells into an afflicted individual. Moreover, such cells can still further be used for the discovery of genes and drugs that are useful for treating certain diseases. For example, novel genes can be identified by differential display or subtractive hybridization or other screening strategies. Still further, pure NEP stem cell populations according to the present invention can be used to generate and screen antibodies that are specific for these specific cells.

In view of the foregoing, it will be appreciated that isolated populations of mammalian neuroepithelial stem cells and lineage restricted glial precursor cells and methods of generating, isolating, and culturing such cells would be a significant advancement in the art.

BRIEF SUMMARY OF THE INVENTION

It is an object of the present invention to provide isolated (pure) populations of mammalian neuroepithelial stem cells and their progeny in feeder-cell-independent adherent cultures.

It is also an object of the invention to provide populations of mammalian lineage-restricted glial precursor cells and their progeny in feeder-cell-independent adherent cultures.

It is another object of the invention to provide methods of generating, isolating, and culturing mammalian neuroepithelial stem cells and lineage restricted glial precursor cells and their progeny.

It is still another object of the invention to provide methods for the growth and regeneration of neuroepithelial stem cells and lineage restricted glial precursor cells in feeder-cell-independent adherent cultures.

It is yet another object of the invention to provide a method for the generation of lineage restricted glial precursor cells from neuroepithelial stem cells.

It is a still further object of the invention to provide pure differentiated populations of cells derived from neuroepithelial stem cells and lineage restricted glial precursor cells.

It is yet another object of the invention to provide cDNA and cDNA libraries from pure differentiated populations derived from neuroepithelial stem cells and lineage restricted glial precursor cells.

It is still another object of the invention to provide antibodies specific to NEP cells and lineage restricted glial precursor cells.

These and other objects can be achieved by providing an isolated, pure population of mammalian CNS neuroepithelial stem cells wherein the cells are capable of self-renewal and proliferation in a feeder-cell-independent adherent culture medium and of differentiation to CNS neuronal or glial cells. Preferably, such neuroepithelial stem cells express nestin, but do not express polysialated neural cell adhesion molecule, glial fibrillary acidic protein, sulfatide, neurofilament, choline acetyl transferase, intermediate filament, ganglioside, or galactocerebroside. It is also preferred that such CNS neuronal cells do not express intermediate filament and neurofilament 68, choline acetyl transferase, glial fibrillary acidic protein, ganglioside, sulfatide, or galactocerebroside. The neuroepithelial stem cells preferably are further capable of differentiation to glial-restricted precursor cells. Such glial-restricted precursor cells are preferably capable of self-renewal and proliferation in a feeder-cell-independent adherent culture medium and of differentiation to CNS glial cells but not to CNS neuronal cells. These glial-restricted precursor cells preferably express nestin and ganglioside, but do not express glial fibrillary acidic protein, sulfatide, or galactocerebroside.

Another illustrative embodiment of the invention comprises an isolated, pure population of mammalian CNS glial-restricted precursor cells, wherein the glial-restricted precursor cells are capable of self-renewal and proliferation in a feeder-cell-independent adherent culture medium and of differentiation to CNS glial cells but not to CNS neuronal cells.

Still another illustrative embodiment of the invention comprises a method of isolating a pure population of mammalian CNS neuroepithelial stem cells wherein the cells are capable of self-renewal in feeder-cell-independent adherent culture medium and of differentiation to CNS neuronal or glial cells, comprising the steps of:

(a) removing a neural tube from a mammalian embryo at a stage of embryonic development after closure of the neural tube but prior to differentiation of cells in the neural tube;

(b) dissociating cells comprising the neural tube removed from the mammalian embryo;

(c) plating the dissociated cells in feeder-cell-independent culture on a substratum and in a medium configured for supporting adherent growth of the neuroepithelial stem cells, wherein the medium comprises effective amounts of fibroblast growth factor and chick embryo extract; and (d) incubating the plated cells at a temperature and in an atmosphere conducive to growth of the neuroepithelial stem cells.

Yet another illustrative embodiment of the invention comprises a method of isolating a pure population of mammalian CNS glial-restricted precursor cells wherein the cells are capable of self-renewal in feeder-cell-independent adherent culture medium and of differentiation to CNS glial cells but not CNS neuronal cells, comprising the steps of:

(a) isolating a population of mammalian CNS neuroepithelial stems cells;

(b) incubating the neuroepithelial stem cells in a medium configured for supporting growth of the neuroepithelial stem cells except for lacking an effective amount of chick embryo extract for a period of time sufficient for the cells to begin differentiating;

(c) subjecting the incubated cells to specific antibody capture using an antibody characteristic of glial-restricted precursor cells to result in a captured subpopulation of cells; and (d) incubating the captured subpopulation of cells in a medium configured for supporting growth thereof comprising effective amounts of fibroblast growth factor and platelet derived growth factor.

Yet another illustrative embodiment of the invention comprises a method of generating a population of mammalian motoneurons comprising the steps of:

(a) isolating a population of mammalian CNS neuroepithelial stems cells;

(b) incubating the neuroepithelial stem cells in a medium that promotes cell proliferation and neuronal differentiation for a period of time sufficient for the cells to begin differentiating; and (c) isolating motoneurons from said differentiating cells. A preferred medium comprises the use of laminin-coated plates and NEP medium lacking an effective amount of chick embryo extract.

DETAILED DESCRIPTION

Figure 1:
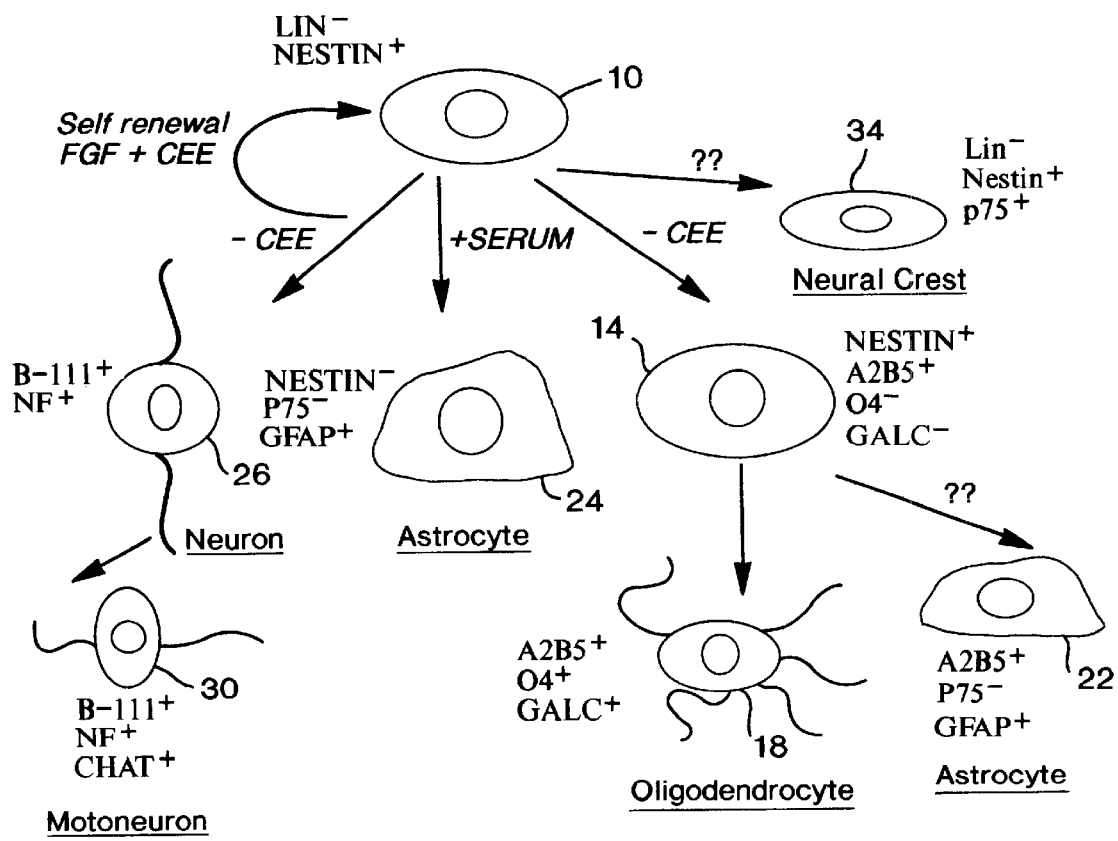
FIG. 1 shows a summary of the antigenic properties of NEP cells and their progeny.

Before the present neuroepithelial stem cells, glial-restricted precursor cells, and methods of making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "an embryo" includes reference to two or more embryos, reference to "a mitogen" includes reference to a mixture of two or more mitogens, and reference to "a factor" includes reference to a mixture of two or more factors.

In describing and claiming the present invention, the following terminology will be used in accordance with the definitions set out below.

As used herein, "self renewal" refers to the capability of a neuroepithelial stem cell to divide to produce two daughter cells, at least one of which is a multipotent neuroepithelial stem cell.

As used herein, "clonal density" and similar terms mean a density sufficiently low enough to result in the isolation of single, non-impinging cells when plated in a selected culture dish. An illustrative example of such a clonal density is about 225 cells/100 mm culture dish.

As used herein, "feeder-cell-independent adherent culture" or similar terms mean the growth of cells in vitro in the absence of a layer of different cells that generally are first plated on a culture dish to which the cells from the tissue of interest are then added. In feeder cell cultures, the feeder cells provide a substratum for the attachment of cells from the tissue of interest and additionally serve as a source of mitogens and survival factors. The feeder-cell-independent adherent cultures herein use a chemically defined substratum, for example fibronectin, and mitogens or survival factors are provided by supplementation of the liquid culture medium with either purified factors or crude extracts from other cells or tissues. Therefore, in feeder-cell-independent cultures, the cells in the culture dish are primarily cells derived from the tissue of interest and do not contain other cell types required to support the growth of cells derived from the tissue of interest.

As used herein, "effective amount" means an amount of a growth or survival or other factor that is nontoxic but sufficient to provide the desired effect and performance. For example, an effective amount of FGF as used herein means an amount selected so as to support self renewal and proliferation of NEP cells when used in combination with other essential nutrients, factors, and the like.

The present invention is illustrated using neuroepithelial stem cells isolated from the rat. The invention encompasses all mammalian neuroepithelial stem cells and is not limited to neuroepithelial stem cells from the rat. Mammalian neuroepithelial stem cells can be isolated from human and non-human primates, equines, canines, felines, bovines, porcines, ovines, lagomorphs, and the like.

The present invention concerns an embryonic spinal cord stem cell, termed NEP cell, derived from caudal neuroepithelium, that requires fibroblast growth factor (FGF) and chick embryo extract (CEE) to proliferate and self renew. NEP cells are characterized by: (1) the expression of nestin, (2) the absence of lineage markers, (3) ability to be maintained in an undifferentiated state in culture, (4) the ability to self renew, and (5) the ability to grow in clonal culture. Under appropriate environmental conditions, NEP cells differentiate into the three principal types of cell in the CNS, neurons, astrocytes, and oligodendrocytes. FIG. 1 presents a model for spinal cord differentiation. This model is similar to that proposed for hematopoiesis and for differentiation of neural crest (see review by D. J. Anderson, The Neural Crest Lineage Problem: Neuropoiesis?, 3 Neuron 1–12 (1989)). According to this model, NEP cells 10 represent a homogeneous population of cells in the caudal neural tube that express nestin (nestin$^+$) but no other lineage marker (lin$^{31}$). These cells divide and self renew in culture and generate differentiated phenotypes. Previous data have suggested intermediate dividing precursors with a more restricted potential. R. H. Miller & V. Szigeti, infra; B. C. Warf et al., supra; N. P. Pringle & W. D. Richardson, supra; J. Ray & F. Gage, Spinal Cord Neuroblasts Proliferate in Response to Basic Fibroblast Growth Factor, 14 J. Neurosci. 3548–64 (1994). Such precursors include those precursors 14 that generate oligodendrocytes 18 and type 2 astrocytes 22, bipotent astrocyte and neuronal precursors (not shown in FIG. 1), as well as neuronal progenitors that generate several kinds of neurons (not shown in FIG. 1). The model therefore suggests that the multipotent precursors (NEP cells) generate differentiated cells (i.e., oligodendrocytes 18, type 2 astrocytes 22, type 1 astrocytes 24, neurons 26, and motoneurons 30) through intermediate precursors. Consistent with this model are the results presented herein showing the existence of cells with a restricted proliferative potential.

FIG. 1 shows that motoneurons arise from a common NEP precursor. The experiments described herein show that low affinity neurotrophin receptor (p75) immunoreactive, choline acetyl transferase (ChAT) positive cells arise in mixed cultures along with other cells of the spinal cord. No clone consisting exclusively of p75/ChAT immunoreactive cells was identified, indicating that, at the age the clones were analyzed, committed motoneuron precursors were not present. The observation that motoneurons arise from a common NEP precursor are consistent with results obtained in chick neural tube experiments. E.g., M. Bronner-Fraser & S. E. Fraser, Cell Lineage Analysis Slows Multipotentiality of Some Avian Neural Crest Cells, 355 Nature 161–64 (1988). These results, together with previous observations, therefore suggest that motoneuron differentiation involves a multipotent precursor undergoing progressive stages of commitment.

NEP cells are similar in some respects to, and yet are clearly different from, neuroepithelial cultures from the myelencephalon and telencephalon. M. Murphy et al., Fibroblast Growth Factor Stimulates the Proliferation and Differentiation of Neural Precursor Cell In Vitro, 25 J. Neurosci. Res. 463–75 (1990); J. Drago et al., Fibroblast Growth Factor-Mediated Proliferation of Central Nervous System Precursors Depends on Endogenous Production of Insulin-like Growth Factor 1, 88 Proc. Nat'l Acad. Sci. USA 2199–2203 (1991); T. J. Kilpatrick & B. F. Bartlett, Cloning and Growth of Multipotential Neural Precursors: Requirements for Proliferation and Differentiation, 10 Neuron 255–65 (1993). Like those cells, NEP cells are FGF-dependent, grow as adherent cells, and require an uncharacterized component present in CEE and/or serum. The cells isolated by Murphy et al., Drago et al., and Kilpatrick and Bartlett differ from NEP cells, however, in that they do not form neurospheres. Thus, brain stem and spinal precursor cells appear to be different from cortical precursors. Brain stem neuroepithelial cells are bipotent and have not been shown to differentiate into oligodendrocytes. Further, spinal cord NEP cells rapidly differentiate into astrocytes in the presence of serum. In contrast, brain stem NEP cells remain in an undifferentiated state in the presence of serum.

NEP cells differ from neural crest stem cells in their morphology and antigenic profile. Neural crest cells are more fibroblastic, tend to be migratory, and avoid cell contact. S. Boisseau et al., A Mammalian In Vitro Model to Study Gangliogenesis from Neural Crest Cells, 85 J. Physiol., Paris 117–22 (1991); P. G. Bannerman & D. Pleasure, Protein Growth Factor Requirements of Rat Neural Crest Cells, 36 J. Neurosci. Res. 46–57 (1993). NEP cells appear more flattened and epithelioid and tend to grow as tightly packed monolayers. Unlike rat neural crest cells, NEP cells do not express immunoreactivity for the low affinity neutrophin receptor (p75; Example 4). Moreover, the progeny of NEP cells differ from neural crest cell derivatives. For example, GFAP-immunoreactive cells from NEP cultures do not express detectable nestin and p75 immunoreactivity (Example 6). In contrast, Schwann cells, which are glial cells of the PNS and differentiate from neural crest, express high levels of both p75 and GFAP in culture. D. L. Stemple & D. J. Anderson, Isolation of a Stem Cell for Neurons and Glia from the Mammalian Neural Crest, 71 Cell 973–85 (1992). Schwann cells also express myelin markers such as O4 and P0, D. L. Stemple & D. J. Anderson, supra; M. S. Rao & D. J. Anderson, The Immortalization of a Neural Crest Stem Cell, ASCB 2098 (1994), which are not expressed by GFAP-immunoreactive cells derived from NEP cultures (e.g. Example 4). NEP cultures contain A2B5 immunoreactive cells, which subsequently express O4, GalC, and O1 immunoreactivity. Cells with this pattern of antigen expression are not viewed as derivatives of neural crest. Further, while neural-crest-derived parasympathetic neurons express ChAT immunoreactivity in vivo, such neurons have not been described from neural crest cultures. D. J. Anderson, supra. NEP cells, however, readily differentiate to generate large numbers of neurons co-expressing p75 and ChAT. Thus, NEP cells and neural crest stem cells are morphologically and antigenically distinct, generate differentiated progeny that are phenotypically different, and therefore represent different stem cells.

Therefore, the NEP stem cells from the developing spinal cord characterized herein have some properties in common with other nervous system stem cells, but are clearly distinct therefrom. NEP cells represent a stem cell population that undergoes self renewal and differentiates into all major CNS phenotypes in culture. NEP cells differ from all previously identified stem cells in their culture conditions and proliferative potential. NEP cell cultures provide a large source of transient cells that can be sorted to obtain differentiated cells types.

The basal medium (NEP medium) used in the experiments described herein comprises DMEM-F12 (GIBCO/BRL, Gaithersburg, Md.) supplemented with 100 $\mu$g/ml transferrin (Calbiochem, San Diego, Calif.), 5 $\mu$g/ml insulin (Sigma Chemical Co., St. Louis, Mo.), 16 $\mu$g/ml putrescine (Sigma), 20 nM progesterone (Sigma), 30 nM selenious acid (Sigma), 1 mg/ml bovine serum albumin (GIBCO/BRL), plus B27 additives (GIBCO/BRL), 25 ng/ml fibroblast growth factor (FGF), and 10% chick embryo extract (CEE). In general, these additives were stored as 100× concentrates at −20° C. until use. Normally, 200 ml of NEP medium was prepared with all additives except CEE and used within two weeks of preparation. CEE was added to the NEP medium at the time of feeding cultured cells.

FGF and CEE were prepared as described in D. L. Stemple & D. J. Anderson, supra; M. S. Rao & D. J. Anderson, supra; L. Sommers et al., Cellular Function of the bHLH Transcription Factor MASH1 in Mammalian Neurogenesis, 15 Neuron 1245–58 (1995), hereby incorporated by reference. FGF is also available commercially (UBI).

Briefly, CEE was prepared as follows. Chick eggs were incubated for 11 days at 38° C. in a humidified atmosphere. Eggs were washed and the embryos were removed and placed in a petri dish containing sterile Minimal Essential Medium (MEM with glutamine and Earle's salts) (GIBCO/BRL) at 4° C. Approximately 10 embryos each were macerated by passage through a 30-ml syringe into a 50-ml test tube. This procedure typically produced about 25 ml of medium. To each 25 ml was added 25 ml of MEM. The tubes were rocked at 4° C. for 1 hour. Sterile hyaluronidase (1 mg/25 g of embryo) (Sigma) was added, and the mixture was centrifuged for 6 hours at 30,000 g. The supernate was collected, passed through a 0.45 $\mu$m filter and then through a 0.22 $\mu$m filter, and stored at −80° C. until use.

Fibronectin (New York Blood Center, New York, N.Y., or Sigma) was diluted to a concentration of 250 $\mu$g/ml in D-PBS (GIBCO/BRL). The fibronectin solution was applied to tissue culture dishes and immediately withdrawn. Collagen (Biomedical Technologies, Inc., Stoughton, Ma.) and poly-L-lysine (Sigma) were each applied to dishes at 20

µg/ml concentrations. Laminin (GIBCO/BRL or Sigma) was used at a concentration of 50–250 µg/ml, and dishes were coated overnight. In some cases, dishes were precoated with pDL (30–70 kDa) (Biomedical Technologies, Inc.). The pDL was dissolved in distilled water and applied to tissue culture plates for an hour, and then the excess pDL was withdrawn and the plates were allowed to air dry. Plates were rinsed with water and then allowed to dry again. The pDL-coated plates were then coated with laminin as described above. NEP cells were dissociated and plated on coated dishes, and their development monitored under several different conditions. Fibronectin was chosen as a growth substrate because NEP cells did not adhere to collagen or poly-L-lysine and adhered poorly to laminin. Thus, all subsequent experiments to maintain NEP cells in culture were performed on fibronectin-coated dishes. Laminin-coated dishes were sometimes used, however, to promote differentiation of NEP stem cells.

EXAMPLE 1

The neural tube undergoes closure at embryonic day 10 in rats, Hamburger, supra, and earliest differentiation occurs a day later, Hamburger, supra; Nornes & Das, supra; Altman & Bayer, supra. Embryonic day 10.5 (E10.5) therefore represents the earliest time point when a large number of undifferentiated NEP cells can be easily isolated. Sprague Dawley rat embryos were removed at E10.5 (13–22 somites) and placed in a petri dish containing Ca/Mg-free Hanks balanced salt solution (HBSS, GIBCO/BRL). The trunk segments of the embryos (last 10 somites) were dissected using tungsten needles, rinsed, and then transferred to fresh HBSS. Trunk segments were incubated at 4° C. in 1% trypsin solution (GIBCO/BRL) for a period of ten to twelve minutes. The trypsin solution was replaced with fresh HBSS containing 10% fetal bovine serum (FBS, GIBCO/BRL). The segments were gently triturated with a Pasteur pipette to release neural tubes free from surrounding somites and connective tissue. Isolated neural tubes were transferred to a 0.05% trypsin/EDTA solution (GIBCO/BRL) for an additional period of ten minutes. Cells were dissociated by trituration and plated at high density in 35 mm fibronectin-coated dishes in NEP medium. Cells were maintained at 37° C. in 5% $CO_2$/95% air. Cells were replated at low density, i.e. p5000 cells per 35 mm plate, one to three days after plating. Cells from several dishes were then harvested by trypsinization (0.05% trypsin/EDTA solution for two minutes). Cells were then pelleted, resuspended in a small volume, and counted. About 5000 cells were plated in a 35 mm dish (Corning or Nunc). For clonal analysis, cells harvested by trypsinization were plated at a density of 50–100 cells per 35 mm dish. Individual cells were identified and located on the dish by marking the position with a grease pencil. Cells were grown in DMEM/F12 with additives, as described above, for a period ranging from 10–15 days.

EXAMPLE 2

E10.5 rat neural tube cells were dissociated according to the procedure of Example 1 except that the cells were plated at low density and incubated in NEP medium with either acidic FGF (aFGF; 25 ng/ml), basic FGF (bFGF; 25 ng/ml), epidermal growth factor (EGF; 50 ng/ml) or no added factor for 48 hours. Cultured cells were fixed and examined by phase contrast microscopy according to methods well known in the art. Cells grown in aFGF or bFGF survived and increased in density. In contrast, no surviving cells were seen in cultures grown without FGF or with 50 ng/ml EGF. Thus, NEP cells require FGF for survival, and EGF does not support growth of NEP cells in adherent culture.

EXAMPLE 3

In this example, E10.5 rat neural tube cells were dissociated according to the procedure of Example 1, and equal numbers of cells were plated at low density in a 35 mm dish and incubated in NEP medium containing bFGF (25 ng/ml) with 10% CEE or without CEE for 5 days. The cultured cells were then fixed and examined by phase contrast microscopy according to methods well known in the art. In the absence of CEE, cells grew slowly and some cells appeared rounded and phase bright. Cells grown in the presence of 10% CEE appeared more homogeneous and proliferated to form a confluent monolayer. Thus, CEE was required to maintain NEP cells in an undifferentiated state. However, CEE in itself was not a survival factor, and NEP cells did not survive in medium supplemented with CEE in the absence of exogenously added FGF. Thus, CEE contains a component distinct from EGF that, in concert with FGF, maintains NEP cells in an undifferentiated state in culture.

EXAMPLE 4

In this example, NEP cells cultured in FGF and CEE on fibronectin-coated plates for 5 days according to the procedure of Example 3, except for the addition of 5-bromodeoxyuridine (BrdU, 1 µM concentration, Sigma) at day 2 to some cells, were tested by immunocytochemistry for cell division and differentiation using a variety of antigenic markers. Nestin is a marker for undifferentiated stem cells. U. Lendahl et al., CNS Stem Cells Express a New Class of Intermediate Filament Protein, 60 Cell 585–95 (1990). BrdU incorporation is a marker for determining the number of dividing cells. The antisera used and their concentrations are summarized in Table 1. All secondary antibodies were obtained from Jackson Immunologicals (Westgrove, Pa.) and were used according to the manufacturer's instructions. Staining procedures were carried out as described in D. L. Stemple & D. J. Anderson, supra. Staining for cell surface antigens was carried out in cultures of living cells. For neurofilament proteins, GFAP and β-III tubulin, cells were fixed with acid-ethanol. For other intracellular antigens, cultures were fixed in 4% formaldehyde for 15 minutes. For BrdU immunocytochemistry, cells were further permeabilized by the procedure of S. P. Memberg & A. K. Hall, Dividing Neuron Precursors Express Neuron-specific Tubulin, 27 Neurobiol. 26–43 (1995), hereby incorporated by reference. Cell cultures were incubated with the selected primary antibody in blocking buffer (PBS, 1 mg/ml bovine serum albumin (BSA), 0.5% triton-X-100, 1% goat serum) for a period of 1 hour, rinsed with PBS, and incubated with a species-specific secondary antibody (Jackson Immunologicals, Westgrove, Pa.) in blocking buffer for an additional hour. Cultures were rinsed with three changes of PBS. Double-labeling and triple-labeling experiments were performed by simultaneously incubating

TABLE 1

| Antibody/Kind | Dilution/Source | Antigen Recognized | Cell type Recognized |
| --- | --- | --- | --- |
| Rat 401/mouse IgG | 1:1/DSHB[a] | Intermediate filament | Stem cells, oligo precursors |
| anti-NCAM/mouse IgG | 1:3/DSHB | Polysialated N-CAM | Neurons |
| anti-β-III tubulin/mouse IgG1 | 1:100/Sigma | Intermediate filament | Neurons |
| anti-neurofilament/mouse IgG2 | 1:100/Sigma | Neurofilament 68 | Neurons |
| anti-ChAT/goat IgG | 1:100/Chemicon[b] | Choline acetyl transferase | Motoneurons |
| anti-glutamate/rabbit IgG | 1:100/Chemicon | Glutamate | CSN neurons |
| anti-GABA/rabbit IgG | 1:100/Chemicon | Gamma amino butyric acid | CNS neurons |
| anti-GFAP/rabbit IgG | 1:500/Accurate | Glial fibrillary acid | Astrocytes |
| anti-A2B5/mouse IgM | 1:3/BMB[c] | Ganglioside | oligodendrocytes and precursors |
| anti-Gal-C/mouse IgG | 1:3/BMB | Galactocerebroside | oligodendrocytes and precursors |
| anti-O4/mouse IgM | 1:1/BMB | Sulfatide | oligodendrocytes |
| anti-O1/mouse IgM | 1:3/BMB | Galactocerebroside | oligodendrocytes |

[a]Developmental Studies Hybridoma Bank, Iowa
[b]Chemicon, Temecula, CA
[c]Boehringer Mannheim Biochemicals, Galthersburg, MD cells in appropriate combinations of primary antibodies followed by non-cross-reactive secondary antibodies.

After 5 days in culture, all cells continued to express nestin, but did not express any other marker tested. Moreover, most of the cells had divided and incorporated BrdU over a three-day period. These results indicate that the cells were dividing and were undifferentiated stem cells. NEP cells passaged at a 1:3 dilution every fifth day as adherent cultures could be maintained as nestin-immunoreactive cells that did not express any markers characteristic of differentiated cells over at least three passages. Subsequent passaging over three months maintained nestin-immunoreactive, lineage-negative cells, but in addition, a small percentage of GFAP-immunoreactive cells (1–5%) could be detected. Thus isolated NEP cells, which express nestin immunoreactivity and lack all lineage specific markers for neuronal and glial sublineages, could be passaged and their numbers amplified when grown under non-differentiation conditions.

EXAMPLE 5

The CNS consists of three major phenotypes, neurons, glia, and astrocytes, all of which express characteristic antigenic markers. To determine if undifferentiated, cultured NEP cells could differentiate into CNS neurons and glia, NEP cells grown on fibronectin in NEP medium for 5 days according to the procedure of Example 1 were harvested by trypsinization and replated on laminin-coated plates in neuroepithelial culture medium without the addition of CEE. Omission of CEE was used to promote differentiation. Laminin was used as a substrate instead of fibronectin because laminin has been shown to promote proliferation and neuronal differentiation. J. Drago et al., supra. After 5 days on laminin-coated plates in NEP medium without CEE, the cells were fixed and processed for determining immunoreactivity to β-III tubulin, neurofilament 160 (NF160), low affinity neurotrophin receptor (p75), and choline acetyl transferase (ChAT), according to the procedure of Example 4. Under these conditions, NEP cells rapidly differentiated, as characterized by alterations in morphology and the expression of lineage-specific antigenic markers.

Small phase bright cells with small processes could be seen as early as 48 hours after replating onto laminin-coated plates in the absence of CEE. Cells with this morphology expressed β-III tubulin immunoreactivity, and a subset of the β-III immunoreactive cells also expressed neurofilament 160 (NF160) immunoreactivity. β-III tubulin immunoreactive, NF160-negative cells were also observed, and these cells likely represent immature neurons. S. P. Memberg & A. K. Hall, supra. The number of β-III tubulin immunoreactive cells increased in culture over a period of 5 days, at which time they represented 20%±4% of the total number of cells.

In addition to the small phase bright, β-III tubulin immunoreactive cells, cells with a larger cell soma and more elaborate processes were also seen. These cells were p75, NF160, and ChAT immunoreactive and were observed both as single cells and as clusters. In the developing neural tube, p75 and ChAT immunoreactivity is characteristic of motoneurons. W. Camu & C. E. Henderson, Purification of Embryonic Rat Motoneurons by Panning on a Monoclonal Antibody to the Low-affinity NGF Receptor, 44 J. Neurosci. Meth. 59–70 (1992). The p75, ChAT immunoreactive cells (hereinafter, "motoneurons") represented a small proportion (4%±2%) of the total number of cells.

EXAMPLE 6

In this example, NEP cells grown on fibronectin in NEP medium for 5 days according to the procedure of Example 1 were harvested by trypsinization and replated on fibronectin-coated plates in NEP medium without CEE but with the addition of 10% FBS for a period of 5 days. Omission of CEE was used to promote differentiation. The cells were then fixed and processed for GFAP, p75, nestin, β-III tubulin, and A2B5 immunoreactivity, according to the procedure of Example 4. Under these conditions, NEP cells rapidly differentiated, and the largest proportion of differentiated cells expressed glial fibrillary acid protein (GFAP) immunoreactivity. After 5 days in culture, GFAP inmmunoreactive cells constituted 73%±6% of the total number of cells present. Two characteristic morphologies could be identified, a flattened, pancake-shaped cell with small or absent processes, and a smaller, more fibroblastic cell with long, elaborate processes. Neither of these two morphologically distinct cells expressed A2B5, p75, or β-III tubulin immunoreactivity, indicating that these cells were most likely type 1 astrocytes. No type 2 astrocytes, as defined by co-expression of A2B5 and GFAP, M. Raff, Glial Cell Diversification in the Rat Optic Nerve, 243 Science 1450–55 (1989); L. E. Lillien & M. C. Raff, Analysis of the Cell-cell Interactions that Control Type-2 Astrocyte Development In Vitro, 4 Neuron 525–34 (1990), were identified, though such type 2 astrocytes have been generated from NEP cells in other culture conditions (e.g. Examples 8 and 12).

EXAMPLE 7

In this example, NEP cells grown on fibronectin in NEP medium for 5 days according to the procedure of Example 1 were harvested by trypsinization and replated on laminin-coated plates in neuroepithelial culture (NEP) medium without the addition of CEE for 5–10 days. Differentiating NEP cells were then labeled, according to the procedure of Example 4, with markers previously identified as being expressed on oligodendrocytes and their precursors: A2B5, GalC, O1, and O4. Three days after replating NEP cells, a subset of the cells began to express A2B5 immunoreactivity. A2B5 immunoreactive cells initially did not express detectable levels of GalC, O4, and O1 immunoreactivity. After an additional three days in culture, however, GalC immunoreactive cells could be seen, which cells also expressed A2B5 immunoreactivity. Such cells appeared flattened and did not have the characteristic morphology of oligodendrocyte-type 2-astrocyte (O2A) progenitors or mature oligodendrocytes. Longer periods in culture, however, allowed more mature-looking oligodendrocytes with a small body and extensive processes to develop. These cells expressed O1 and GalC immunoreactivity, markers characteristic of differentiated oligodendrocytes. Thus, NEP cells can generate oligodendrocytes that mature over 10 days in culture. The pattern of antigen expression further suggests the existence of a dividing oligodendrocyte precursor that subsequently generates oligodendrocytes, as has been described from spinal cord cultures from older embryos. B. C. Warf et al., supra; R. H. Miller & V. Szigeti, Clonal Analysis of Astrocyte Diversity in Neonatal Spinal Cord Cultures, 115 Development 133–42 (1991).

Therefore, as shown in Examples 5–7, NEP cells grown in culture generate neurons, glia, and oligodendrocytes when replated on laminin in the absence of CEE. This culture condition, while suboptimal for any particular phenotype, is sufficient to generate differentiated progeny and has been used to assess differentiation in subsequent experiments.

EXAMPLE 8

NEP cells grown in culture could be either a homogeneous population of cells where each cell could differentiate into all phenotypes or a heterogeneous population of cells with a variety of differentiation potentials. To distinguish between these possibilities, cultured NEP cells were grown at clonal density, individual cells were circled, and their development followed for a period of 15 days. Clones were analyzed for differentiation by triple labeling using GFAP, β-III tubulin, and A2B5 as markers for astrocytes, neurons, and oligodendrocyte precursors.

For preparation of clonal cultures of neuroepithelial cells, NEP cells prepared according to the procedure of Example 1 were trypsinized and plated in 35 mm dishes coated with fibronectin at a dilution of about 50 cell/dish. In some experiments, however, cells were plated at about 10 cells/dish. Cells were allowed to settle for a period of 4 hours, and then single cells were circled and their development followed in culture. In most experiments, clonal cultures were terminated after 12 days. In experiments to demonstrate oligodendrocyte development, clones were observed for 18–21 days.

For replating individual clones, a glass cloning ring (Fisher Scientific, Pittsburg, Pa.) was placed around each clone and the cells isolated by trypsinization for 1–2 minutes with 100 µl of trypsin/EDTA solution. Cells were resuspended in fresh medium, and an aliquot of cells (50–100 cells) was replated onto fibronectin-coated cultures dishes. Single cells were identified and circled with a grease pencil and their development followed as described above.

Primary or replated clonal culture plates were usually triple labeled with the cell surface antigen and the appropriate secondary antibody being used in live cell culture according to the procedures described in Example 4. Clones were then fixed in 4% paraformaldehyde for 10 minutes and processed sequentially for the other antigens. The diaminobenzidine (DAB, Sigma) reaction to horseradish peroxidase labeled secondary antibodies was always performed after all other staining had been completed because reduced staining with some antigens was observed if the clones were processed for DAB histochemistry first.

At least some clones were stained by all three markers and thus contained all three phenotypes of cells. Thus, at least some NEP cells are capable of generating neurons, astrocytes, and oligodendrocytes. To confirm that A2B5 immunoreactive cells represented oligodendrocytes, some clones were restained with O1 or GalC. The results summarized in Table 2 represent 256 colonies from three independent clonal assays.

TABLE 2

| Antigen Expressed | % of Clones |
| --- | --- |
| A2B5 + β-III tubulin | 13 ± 2 |
| A2B5 + GFAP | 28 ± 2 |
| A2B5 + β-III tubulin + GFAP | 42 ± 3 |
| GFAP + β-III tubulin | 17 ± 1 |
| GFAP alone | None |
| β-III tubulin alone | None |
| A2B5 alone | None |

All clones analyzed contained more than one phenotype. Neuron and oligodendrocyte clones, as well as neuron and astrocyte clones were identified. A significant proportion of NEP cells generated colonies containing all three phenotypes of cells. In all cases, when clones were carefully studied, it was possible to identify cells that did not express any of the markers tested, suggesting that precursor cells were still present. Further, no clones that contained only one cell type could be identified, suggesting that at this stage no committed precursors were present in culture.

EXAMPLE 9

To determine if multipotent stem cells underwent self renewal, NEP cells prepared according to the procedure of Example 1 were plated at low density and single cells were observed for 10 days according to the procedure of Example 8. Clones at this stage varied in size from about 100 to several thousand cells. The largest clones were identified, harvested by trypsinization, and a subset of cells was replated on fibronectin-coated plates in NEP medium. Individual cells from each parent clone were circled and observed in culture. Fifteen days after replating, clones were triple labeled for O1, β-III tubulin, and GFAP expression. The number of daughter clones that expressed all three markers is shown in Table 3, which contains the pooled results from three independent NEP cell preparations.

TABLE 3

| Clone No. | No. of Cells Observed | No. of Multipotent Daughter Clones |
|---|---|---|
| 1 | 40 | 15 |
| 2 | 34 | 3 |
| 3 | 38 | 12 |
| 4 | 36 | 8 |
| 5 | 42 | 9 |
| 6 | 22 | 2 |
| 7 | 21 | 3 |
| 8 | 13 | 1 |
| 9 | 17 | 8 |
| 10 | 21 | 7 |
| 11 | 19 | 3 |
| 12 | 23 | 4 |
| 13 | 41 | 13 |
| 14 | 16 | 7 |
| 15 | 37 | 9 |

Of the 15 clones that were followed, each contained 1–15 daughter clones (3–50% of replated cells) that had differentiated into neurons, astrocytes, and oligodendrocytes. Thus, all of the clones that were observed generated multipotent daughter cells. Therefore, individual NEP cells are capable of self renewal.

EXAMPLE 10

Stem cells that undergo self renewal and retain their ability to differentiate into multiple phenotypes have been previously described. B. A. Reynolds et al., A Multipotent EGF-responsive Striatal Embryonic Progenitor Cell Produces Neurons and Astrocytes, 12 J. Neurosci. 4565–4574 (1992); B. A. Reynolds et al., Clonal and Population Analysis Demonstrate that an EGF-responsive Mammalian Embryonic CNS Precursor is a Stem Cell, 175 Develop. Biol. 1–13 (1996); A. L. Vescovi et al., bGFG Regulates the Proliferative Fate of Unipotent (Neuronal) and Bipotent (Neuron/Astroglial) EGF-generated CNS Progenitor Cells, 11 Neuron 951–66 (1993); T. J. Kilpatrick & B. F. Bartlett, supra; T.J. Kilpatrick & B. F. Bartlett, Cloned Multipotential Precursors from the Mouse Cerebrum Require FGF-2 whereas Glial Restricted Precursors are Stimulated by either FGF-2 or EGF, 15 J. Neurosci. 3653–61 (1995); A. A. Davis & S. Temple, A Self Renewing Multipotential Stem Cell in Embryonic Rat Cerebral Cortex, 372 Nature 263–66 (1994); S. Temple & A. Davis, Isolated Rat Cortical Progenitor Cells are Maintained in Division In Vitro by Membrane Associated Factors, 120 Development 999–1008 (1994). One such stem cell is the neurosphere isolated from cortical ventricular zone, which can be maintained in an undifferentiated state over multiple passages in defined medium in the presence of EGF. B. A. Reynolds et al. (1992), supra; B. A. Reynolds et al. (1996), supra; A. L. Vescovi et al., supra. To determine if NEP cells could be grown as neurospheres, cells grown in adherent cultures according to the procedure of Example 1 were trypsinized, pelleted, and grown in bacterial plates as suspension cultures at a density of 100–300 cells, i.e. in non-adherent culture at clonal density. The medium used was NEP medium. Most cells did not survive replating, but, on average, 2.5±1.0 cells (1.2%) formed neurospheres. No neurospheres were obtained when cells were grown in NEP medium in which EGF (50 ng/ml) was substituted for FGF (20 ng/ml).

Neurospheres generated in FGF-containing medium were replated onto either fibronectin-coated dishes in non-differentiating medium or onto laminin-coated plates in differentiating medium (NEP medium minus CEE). Spheres grown on fibronectin were labeled with BrdU and nestin, showing that the majority of cells consisted of undifferentiated nestin-immunoreactive, dividing cells. Such undifferentiated cells appeared morphologically similar to NEP cells that were generated from neural tube dissociation, and could be passaged and used to generate additional neurospheres. Spheres grown on laminin were triple labeled for O1, β-III tubulin, and GFAP expression, showing that neurospheres can differentiate into neurons, astrocytes, and oligodendrocytes. Thus, NEP cells and FGF-dependent neurospheres represent identical cells grown under adherent or non-adherent culture conditions, respectively, but are distinct from the EGF-dependent neurospheres generated from older embryos.

EXAMPLE 11

Motoneurons are the earliest cell type to differentiate from caudal neuroepithelium. E.g. Hamburger, supra. N-CAM (neural cell adhesion molecule) and p75 immunoreactive neurons are seen in vivo and in vitro within 12 hours of the time that neural tubes are isolated and NEP cells placed in culture. E. W. Chen & A. Y. Chiu, supra; W. Camu & C. E. Henderson, supra. It is therefore possible that a committed motoneuron precursor was already present at the time NEP cells were placed in culture. To determine if such a precursor existed, NEP clonal cultures were analyzed with motoneuron and other lineage-specific markers. E10.5 NEP cells were isolated and cultured on fibronectin-coated dishes for 5 days, harvested by trypsinization, and replated onto fibronectin-coated 35 mm dishes at clonal density in NEP medium with CEE, according to the procedure of Example 8. Single isolated cells were circled and observed for a period of 10–21 days. Clones were then either (a) double-labeled for ChAT and either β-III tubulin, GFAP, or A2B5, or (b) triple-labeled for ChAT, β-III tubulin, and A2B5 expression, according to the procedure of Example 4. Clones were then scored for the markers they expressed. These results are summarized in Table 4.

TABLE 4

| Antigen Expressed | Proportion of Clones (%) |
|---|---|
| ChAT + β-III tubulin | 26/28 (93%) |
| ChAT + GFAP | 30/32 (94%) |
| ChAT + A2B5 | 24/27 (89%) |

Table 4 represents the data from 87 clones and shows the number of clones expressing both markers when double-labeled. No clones were observed that contained only ChAT immunoreactive cells, thus no clone containing motoneurons alone was observed. Motoneuron-containing clones also contained astrocytes, other neurons, and/or oligodendrocytes. These results are evidence, therefore, that there is a common progenitor that can generate motoneurons and other spinal cord cells.

Glial Restricted Precursors Derived from NEP Stem Cells

Multipotent NEP stem cells can be induced to generate self-renewing precursor cells restricted to subsequent glial differentiation. The self-renewing precursor population can be isolated by immunopanning using the monoclonal antibody A2B5 and can be maintained in an undifferentiated state over multiple divisions when grown in platelet derived growth factor (PDGF) and bFGF. A2B5$^+$ cells differ from parental NEP cells in antigenic phenotype and differentiation potential. A2B5$^+$ cells lack the ability to differentiate into neurons under conditions that promote neuronal differentiation in NEP cells. A2B5$^+$ cells retain, however, the ability to differentiate into oligodendrocytes and astrocytes and are thus identified as multipotential glial-restricted precursors.

Figure 2:
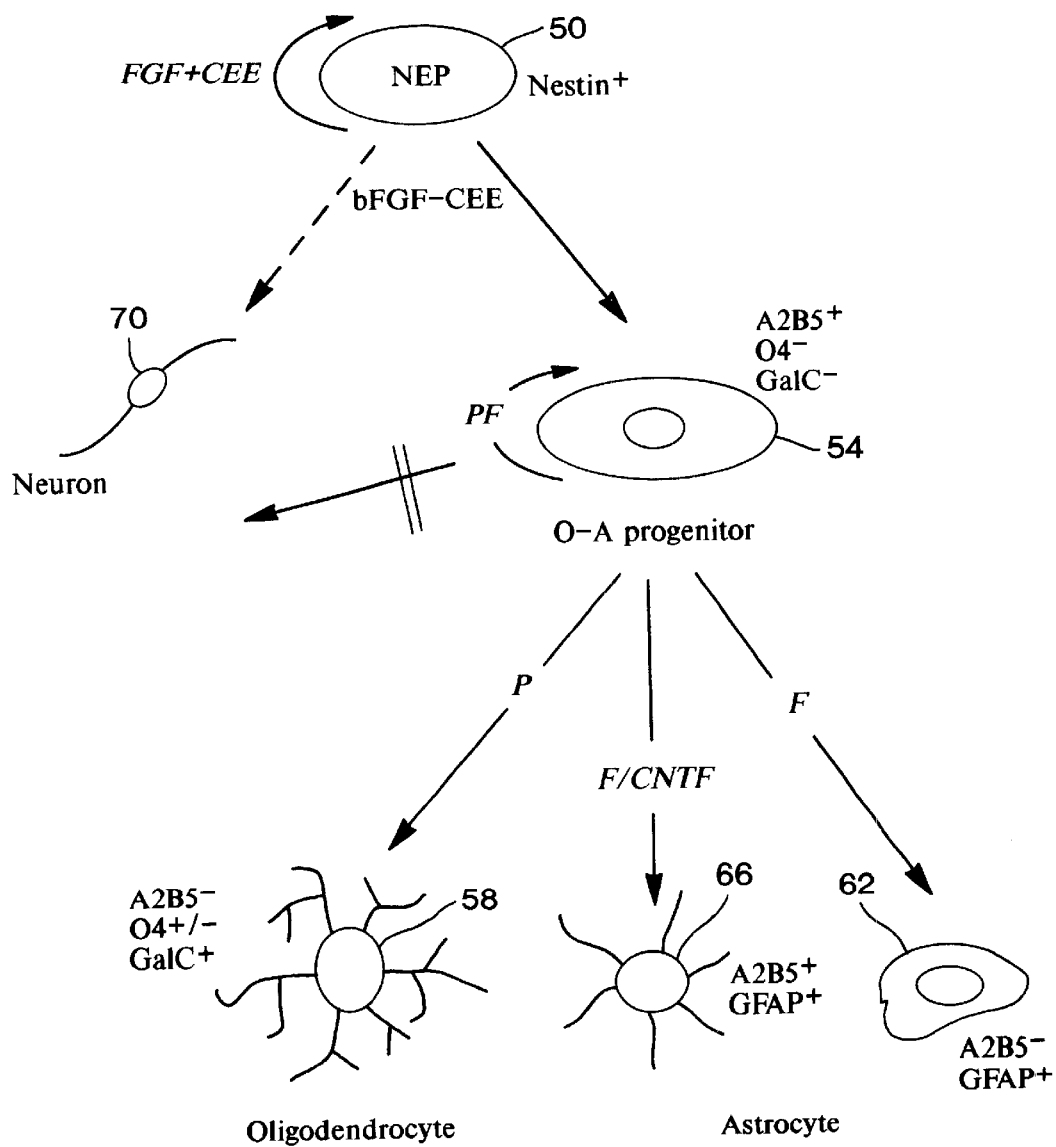
FIG. 2 shows a summary of the antigenic properties of multipotent NEP stem cells, glial-restricted A2B5$^+$ cells (oligodendrocyte-astrocyte (O-A) progenitor) that arise from NEP cells, and oligodendrocytes and astrocytes that arise from the O-A progenitor.

FIG. 2 shows a model of NEP cell differentiation, wherein multipotent NEP cells 50 have the capability to differentiate into an oligodendrocyte-astrocyte (O-A) progenitor 54 that is capable of self-renewal and also retains the capability to further differentiate into oligodendrocytes 58, type 1 astrocytes 62, and type 2 astrocytes 66. FIG. 2 also illustrates that NEP cells are capable of differentiating into neurons 70, whereas O-A progenitor cells are not.

Several lines of evidence show that A2B5 immunoreactive glial-restricted precursors arise from multipotent NEP cells. First, NEP cells are a homogeneous nestin-positive, A2B5 -negative population of cells (Example 4). Second, clonal analysis of NEP cell cultures reveals no clones that give rise to only glial cells (Example 8). Third, A2B5$^+$ cells always arise in clones that contain A2B5$^-$ neurons and astrocytes (Example 8). Thus, there is no evidence that NEP cells contain a committed A2B5$^-$, O-2A progenitor. Rather, a process of differentiation occurs where an NEP cell transits to a more restricted cell type.

The A2B5$^+$ population derived from NEP cells appears homogeneous and uniformly lacks the ability to generate neurons. These A2B5$^+$ cells share some similarities with, but are also different from, other glial restricted precursors identified in the CNS. F. Aloisi et al., Developmental Appearance, Antigenic Profile, and Proliferation of Glial Cells of the Human Embryonic Spinal cord: An Immunocytochemical Study Using Dissociated Cultured Cells, 5 Glia 181–81 (1992); H. M. Blau & S. M. Hughes, Cell Lineage in Vertebrate Development, 2 Curr. Biol. 981–85 (1990); R. S. Cameron & P. Rakic, Glial Cell Lineage in Cerebral Cortex: A Review and Synthesis, 4 Glia 124–37 (1991); C. L. Chan et al., Oligodendrocyte-type 2 Astrocyte (O-2A) Progenitor Cells from Neonatal and Adult Rat Optic Nerve Differ in Their Responsiveness to Platelet-Derived Growth Factor, 55 Brain Res. Dev. Brain Res. 275–82 (1990); P. Cochard & M. C. Giess, [Oligodendrocyte Lineage], 189 C R Seances Soc. Biol. Fil. 263–69 (1995); A. A. Davis & S. Temple, supra; G. A. Elder et al., Characterization of Glial Subpopulations in Cultures of the Ovine Central Nervous System, 1 Glia 317–27 (1988); J. Fok-Seang & R. H. Miller, Distribution and Differentiation of A2B5$^+$ Glial Precursors in the Developing Rat Spinal Cord, 37 J. Neurosci. Res. 219–35 (1994); B. P. Fulton et al., Visualization of O-2A Progenitor Cells in Developing and Adult Rat Optic Nerve by Quisqualate-Stimulated Cobalt Uptake, 12 J. Neurosci. 4816–33 (1992); D. S. Galileo et al., Neurons and Glia Arise from a Common Progenitor in Chicken Optic Tectum: Demonstration with Two Retroviruses and Cell Type-Specific Antibodies, 87 Proc. Nat'l Acad. Sci. USA 458–62 (1990); A. L. Gard et al., Oligodendroblasts Distinguished from O-2A Glial Progenitors by Surface Phenotype (O4+GalC−) and Response to Cytokines Using Signal Transducer LIFR Beta, 167 Dev. Biol. 596–608 (1995); R. Hardy & R. Reynolds, Proliferation and Differentiation Potential of Rat Forebrain Oligodendroglial Progenitors Both In Vitro and In Vivo, 111 Development 1061–80 (1991); R. J. Hardy & V. L. Friedrich, Jr., Oligodendrocyte Progenitors Are Generated Throughout the Embryonic Mouse Brain, But Differentiate in Restricted Foci, 122 Development 2059–69 (1996); P. E. Knapp, Studies of Glial Lineages and Proliferation In Vitro Using an Early Marker for Committed Oligodendrocytes, 30 J. Neurosci. Res. 33645 (1991); M. B. Luskin et al., Neurons, Astrocytes, and Oligodendrocytes of the Rat Cerebral Cortex Originate from Separate Progenitor Cells: An Ultrastructural Analysis of Clonally Related Cells, 13 J. Neurosci. 1730–50 (1993); R. H. Miller, Oligodendrocyte Origins, 19 TINS 92-96 (1996); K. Ono et al., Early Development and Dispersal of Oligodendrocyte Precursors in the Embryonic Chick Spinal Cord, 121 Development 1743–54 (1995); M. C. Raff et al., A Glial Progenitor Cell That Develops In Vitro into an Oligodendrocyte Depending on Culture Medium, 303 Nature 390–96 (1983); M. J. Rivkin et al., Oligodendroglial Development in Human Fetal Cerebrum, 38 Ann. Neurol. 92–101 (1995); P. M. Wood & A. K. Williams, The Generation of Neurons and Oligodendrocytes from a Common Precursor Cell, 7 Neuron 685–93 (1984). NEP-derived A2B5$^+$ cells share several characteristics with optic-nerve-derived O-2A progenitor cells, including morphology, migratory nature, responsiveness to PDGF and bFGF, and the ability to generate oligodendrocytes and type-2 astrocytes. In contrast to postnatal O-2A progenitor cells, however, NEP-derived A2B5$^+$ cells can also give rise to type 1 astrocytes. It thus appears that A2B5$^+$ cells purified from NEP cells represent an earlier stage of glial precursor cell development than the A2B5$^+$ O-2A progenitor cells that have been studied so extensively.

Therefore, the presently described invention provides direct evidence for a lineage relationship between multipotent and lineage-restricted precursor cell populations and identifies morphological, antigenic, and cytokine dependence data to distinguish between the two populations. Moreover, there is established an accessible culture system to follow the development of isolated precursor cells and to study the cellular and molecular events that regulate differentiation processes.

EXAMPLE 12

Neurons, oligodendrocytes, and astrocytes can be identified using a variety of lineage specific markers. G. S. Eisenbarth et al., Monoclonal Antibody to Plasma Membrane Antigen of Neurons, 76 Proc. Nat'l Acad. Sci. USA 4913–17 (1979); E. E. Geisert & A. Frankfurter, The Neuronal Response to Injury As Visualized by Immunostaining of Class P-tubulin in the Rat, 102 Neurosci. Lett. 137–41 (1989); I. Sommer & M. Schachner, Monoclonal Antibody (O1-O4) to Oligodendrocyte Cell Surfaces: An Immunocytological Study in the Central Nervous System, 83 Dev. Biol. 311–27 (1981); P. A. Trimmer et al., Combination of In Situ Hybridization and Immunocytochemistry to Detect Messenger RNAs in Identified CNS Neurons and Glia in Tissue Culture, 39 J. Histochem. Cytochem. 891–98 (1991). Table 5 shows the lineage specific markers used in the present example.

TABLE 5

Antibodies That Identified Specific Cell Types

| Antibody | Antigen | Cell Type |
| --- | --- | --- |
| A2B5 mouse IgM, 1:2 | gangliosides | Glial precursors |
| O4 mouse IgM, 1:2 | galactoside | Oligodendrocytes/precursors |
| α-GalC mouse IgG, 1:2 | galactocerebroside | Oligodendrocytes |
| α-GFAP rabbit IgG, 1:500 | glial fibrillary acid | Astrocytes |
| α-β-III tubulin mouse IgG, 1:400 | intermediate filament | Neurons |
| RT-97 mouse IgG, 1:5 | neurofilament | Neurons |

In addition to defining differentiated cells, some precursor cells can also be recognized by specific antibodies. Two such markers were used herein, nestin and A2B5. Nestin is expressed by a variety of undifferentiated cells in the CNS. E.g., U. Lendahl et al., supra. The A2B5 antibody labels O2A progenitor cells.

In this example, NEP cells prepared from E10.5 rat neural tube cells according to the procedure of Example 1 were grown in the presence of CEE and bFGF for 3 days and were then replated at 5000 cells/coverslip in NEP medium devoid of CEE for an additional 5 days. Cells were incubated for 24 hours with BrdU and stained with anti-BrdU according to the procedure of Example 4. Parallel cultures were double stained after 7 days with selected combinations of the antibodies described in Table 5. Seventy percent of NEP cells cultured in the absence of CEE for three days exhibited A2B5 immunoreactivity. These A2B5$^+$ cells had a flat morphology and were able to divide in the presence of bFGF. After 4 days in culture in the absence of CEE, 81%±7% of the A2B5$^+$ NEP-derived cells were engaged in cell division as determined by anti-BrdU immunoreactivity. Double labeling of the NEP-derived A2B5+ cells with the antibodies α-nestin, α-GalC, α-GFAP, α-β-III tubulin, and α-p75 (an antibody against the low affinity NGF receptor that recognizes a subset of astrocytes) showed that none of the lineage markers were coexpressed on A2B5$^+$ cells. A substantial subset of the A2B5$^+$ cells, however, expressed α-nestin. This coexpression of α-nestin and A2B5 has been previously described on O-2A progenitor cells. Thus, NEP-derived A2B5-positive cells are antigenically similar to O-2A progenitor cells.

After an additional 2 days in culture, A2B5$^+$ cells had begun to express glial-specific markers. A subpopulation of cells was clearly GalC$^+$ by that time. To confirm that cells were sequentially differentiating into oligodendrocytes, cultures were stained with O4 and α-GalC. As expected, 30% of the O4$^+$ cells coexpressed α-GalC, resembling immature oligodendrocytes. Double labeling with A2B5 and αGFAP showed that 10% of the A2B5$^+$ cells were also GFAP$^+$, resembling the antigenic characteristic of type-2 astrocytes. All the markers that were coexpressed at that later time point on a subset of A2B5$^+$ cells are characteristic of cells belonging to the O-2A lineage. These results suggested that at least a subset of the A2B5$^+$ cells represented glial precursor cells and that A2B5 was a useful marker to define this subpopulation of cells in more detail.

EXAMPLE 13

To determine whether A2B5$^+$ cells arise from multipotent NEP cells or whether A2B5$^+$ cells arise from an already committed subpopulation of A2B5$^-$ NEP cells, NEP cells were plated at clonal densities according to the procedure of Example 8, and their development in culture was followed for 10 days. Cells were then double stained with the antibody combinations A2B5/α-β-III tubulin or A2B5/α-GFAP. The results of analysis of 132 clones are summarized in Table 6.

TABLE 6

| Antigen expressed | % of Clones | No. of Clones |
|---|---|---|
| A2B5$^+$/β-III tubulin$^+$ | 93% | 71/76 |
| A2B5$^+$/GFAP$^+$ | 91% | 51/56 |
| A2B5$^+$ alone | 0 | 0/132 |

Nearly all of the 132 clones consisted of a mixture of A2B5$^+$, GFAP$^+$, and β-III tubulin$^+$ cells. Ninety-one percent of the clones contained cells that were either A2B5$^+$ or GFAP$^+$, while 93% of the clones were either A2B5$^+$ or β-III tubulin$^+$. None of the analyzed clones consisted only of cells that were A2B5$^+$. It is noteworthy that although at this early stage none of the clones contained GalC$^+$ cells, oligodendrocytes could be identified in clonal cultures and in mass culture at later stages (12–15 days after plating on medium devoid of CEE). These clonal analyses suggest that the A2B5$^+$ population arose from a common multipotential A2B5$^-$ precursor cell.

EXAMPLE 14

To determine directly whether NEP-derived A2B5$^+$ cells can only give rise to glial cells, the A2B5$^+$ population was purified by specific antibody capture assay (immunopanning). L. J. Wysocki & V. L. Sato, Panning for Lymphocytes: A Method for Cell Selection, 75 Proc. Nat'l Acad. Sci. 2844–48 (1978); M. Mayer et al., Ciliary Neurotrophic Factor and Leukemia Inhibitory Factor Promote the Generation, Maturation, and Survival of Oligodendrocytes, 120 Development 142–53 (1994), hereby incorporated by reference. Briefly, cells prepared according to Example 1 were trypsinized and the suspension was plated on an A2B5-antibody-coated dish to allow binding of all A2B5$^+$ cells to the plate. The supernate was removed, and the plate was washed with DMEM supplemented with additives (DMEM-BS) described by J. E. Bottenstein & G. H. Sato, Growth of Rat Neuroblastoma Cell Line in Serum-Free Supplemented Medium, 76 Proc. Nat'l Acad. Sci. USA 514–17 (1979), hereby incorporated by reference. The bound cells were scraped off and plated on fibronectin/laminin coated glass coverslips in 300 μl DMEM-BS±growth factors at 5000 cells/well. In the final culture, the contaminating A2B5$^-$ cells represented less than 10% of the total cells. The A2B5 antibody for coating the plates was used at a concentration of 5 μg/ml protein. Cells were allowed to bind to the plate for 20–30 minutes in a 37° C. incubator. Growth factors were added every other day at a concentration of 10 ng/ml. Recombinant human PDGF-AA was obtained from Chiron Corporation. Recombinant rat ciliary neurotrophic factor (CNTF) was obtained from Precision Research Biochemicals. Recombinant bFGF was purchased from PeroTech Inc., and retinoic acid (RA) was from Sigma.

After 5 days of culturing NEP cells in the absence of CEE, cells were immunopurified, plated on fibronectin/laminin coated dishes, and exposed to cytokines previously associated with differentiation of precursor into oligodendrocytes, astrocytes, or neurons. The A2B5-panned population was >98% positive for A2B5$^+$ cells when stained one hour after panning. Staining 24 hours after plating showed that all cells of the panned population were A2B5$^+$ and did not express any other lineage markers tested.

Panned cultures in the presence of bFGF and no other growth factors for 5 days consisted of 1% oligodendrocytes, 50% GFAP$^+$ astrocytes, and 49% A2B5$^+$ cells. The proportion of differentiated cells was significantly shifted when the bFGF-containing medium was replaced after 3 days with medium supplemented only with PDGF. Under these conditions, the culture consisted of 30% oligodendrocytes, 50% astrocytes, and 20% A2B5$^+$ cells.

Although growth in the presence of bFGF alone was sufficient to allow differentiation of NEP cells into neurons in the parent population, no neurons were detected in the A2B5$^+$ panned population cultured in the presence of bFGF. To enhance the probability of neuronal differentiation, the medium was additionally supplemented with retinoic acid, which significantly increased neuronal differentiation in the parent NEP cell population. Even in this neuron-promoting environment, the immunopurified A2B5$^+$ population did not contain β-III tubulin$^+$ cells. It was unlikely that the neuronal population was lost through selective cell death, because no significant cell death was observed in the panned mass cultures at any time, suggesting that neurons did not appear rapidly and die. Moreover, no evidence of β-III tubulin$^+$ ghosts was detected.

These results suggest that the precursor cells that are responsible for generating neurons were not part of the immunopurified A2B5$^+$ population. As the A2B5-panned cells gave rise to astrocytes and oligodendrocytes, but not to neurons, it appeared that the A2B5$^+$ population contained precursor cells that were restricted to glial lineage.

EXAMPLE 15

Mass culture experiments suggested that the A2B5-panned population prepared according to Example 14 contained cells with a differentiation potential restricted to glial lineages. This experiment, however, did not address whether astrocytes and oligodendrocytes are generated from committed unipotential cells present in the A2B5$^+$ population or whether single cells are bipotential and can generate both astrocytes and oligodendrocytes. To address this question, clonal experiments were performed, wherein the A2B5-panned population was stained with A2B5 1 day after panning, and cells were plated at limiting dilution in 96-well plates. Wells were scored with immunofluorescence, and wells with one A2B5$^+$ stained cell were recorded and cultured in PDGF/bFGF for 7 days. This procedure allowed the expansion of clones and also minimized the amount of cell death occurring when single cells were directly plated into differentiation conditions. After 7 days, expanded clones contained from 50–200 cells and were uniformly A2B5$^+$.

The majority of the clones (51) were first washed with bFGF-free DMEM-BS and then switched to PDGF-supplemented medium, an effective culture condition to induce oligodendrocyte generation, as shown in mass culture experiments. All clones contained oligodendrocytes, GFAP$^+$ astrocytes, and A2B5$^+$ cells, while none of the clones contained β-III tubulin$^+$ cells, suggesting that single A2B5$^+$ cells were at least bipotential and also were restricted to glial cell lineages (Table 7).

TABLE 7

| Marker expressed | Growth Condition | |
| --- | --- | --- |
|  | PDGF | FGF/CNTF |
| A2B5$^+$/GFAP$^+$ | 0 | 6 |
| A2B5$^+$ | 51 | 6 |
| GFAP$^+$ | 51 | 4 |
| GalC$^+$ | 51 | 1 |
| β-III tubulin$^+$ | 0 | 0 |
| Total No. of Clones | 51 | 6 |

The differentiation potential of A2B5$^+$ cells in a culture medium supplemented with bFGF and CNTF was also tested. From the panned mass culture experiments it seemed clear that bFGF alone leads to an increase in the number of GFAP$^+$ astrocytes and a decrease in the number of oligodendrocytes. Depending on culture conditions, CNTF has been shown to promote oligodendrocyte generation, M. Mayer et al., supra, or to lead to the generation of type-2 astrocytes, which are GFAP$^+$ and transiently express A2B5. L. E. Lillien & M. C. Raff, Differentiation Signals in the CNS: Type-2 Astrocyte Development In Vitro as a Model System, 5 Neuron 5896–6273 (1990). Six clones were analyzed that were expanded in PDGF/bFGF and then switched to bFGF/CNTF. Surprisingly, all six clones contained cells that were A2B5$^+$/GFAP$^+$, resembling the type-2 astrocyte phenotype. Only 1 clone contained GalC$^+$ oligodendrocytes, and no clone contained β-III tubulin$^+$ cells. This result suggested that in the presence of CNTF and bFGF, A2B5$^+$ cells predominantly differentiate into cells with a type-2 astrocyte phenotype.

Five A2B5$^+$ clone were analyzed in different neuron-promoting conditions and, as before, were unable to generate neurons. Five PDGF/bFGF expanded clones were trypsinized, divided into two portions and replated into either bFGF alone or bFGF supplemented with retinoic acid. Clones were stained with the antibodies A2B5, α-GFAP, α-GalC, and α-β-III tubulin (Table 8).

TABLE 8

| Marker expressed | Growth Condition | |
| --- | --- | --- |
|  | FGF | FGF/RA |
| A2B5$^+$/GFAP$^+$ | 0 | 6 |
| A2B5$^+$ | 5 | 5 |
| GFAP$^+$ | 5 | 5 |
| GalC$^+$ | 1 | 0 |
| β-III tubulin$^+$ | 0 | 0 |
| Total No. of Clones | 5 | 5 |

None of the clones, regardless of whether cells were grown in bFGF alone or bFGF/RA, contained β-III tubulin immunoreactivity. In contrast, all five clones consisted of a mixture of cells that were either A2B5$^+$ or GFAP$^+$, but not both. Only one clone grown in bFGF alone contained GalC immunoreactive oligodendrocytes, whereas in bFGF/RA, no GalC$^+$ oligodendrocytes were found. These data support the initial observation, that A2B5$^+$ cells isolated from induced NEP cell cultures were multipotential and restricted in their differentiation potential to cells of the glial lineages.

EXAMPLE 16

To fulfill the criteria of a true intermediate precursor, cells need to have an extended self-renewal capacity without losing the ability to differentiate into more than one specific cell type. To test the self-renewal capacity of individual A2B5$^+$ cells, two clones expanded in PDGF/bFGF for 7 days were selected for long-term culture and passaging. The two clones were refed every other day with PDGF/bFGF and maintained for a total of 3 months with 4 serial passages. Clones were grown in PDGF/bFGF, as this combination of cytokines apparently inhibited differentiation and promoted division. Cells were stained before and after each passage and were negative for all differentiation markers tested, except for A2B5$^+$, at all time points.

To determine the differentiation potential of long term clones, during each passage single cells were replated, re-expanded to 50–200 cells, and switched to PDGF alone to promote differentiation. In these secondary cultures, oligodendrocytes and astrocytes appeared consistently after 8–10 days. The ability to differentiate into oligodendrocytes and astrocytes was not altered significantly with increased passages, suggesting that these long-term propagated cells were still multipotential.

These results show that A2B5$^+$ cells that differentiate from multipotent NEP cells can be expanded and propagated as precursor cells. Passaged individual A2B5+ cells self renew and are able to generate oligodendrocytes, A2B5+ and A2B5− astrocytes, but not neurons. NEP-derived A2B5+ cells thus represent multipotential intermediate precursor cells restricted to glial lineages.

All of the references cited herein and not previously expressly incorporated by reference are hereby incorporated by reference.

We claim:

1. An isolated, pure, homogeneous population of neuroepithelial stem cells derived from the neural tube from a rat embryo at a stage of embryonic development after closure of the neural tube which require fibroblast growth factor for proliferation and self-renewal and which differentiate into CNS neuronal cells and CNS glial cells, comprising oligodendrocytes, A2B5-positive astrocytes and A2B5-negative astrocytes.

2. The population of claim 1 wherein said neuroepithelial stem cells express nestin immunoreactivity, but do not express polysialated neural cell adhesion molecule, glial fibrillary acid protein, sulfatide, neurofilament, choline acetyl transferase, intermediate filament, ganglioside, or galactocerebroside immunoreactivities.

3. The population of claim 1 wherein said CNS neuronal cells express intermediate filament and neurofilament 68 immunoreactivities upon differentiation from said neuroepithelial stem cells.

4. The population of claim 3 wherein said CNS neuronal cells express choline acetyl transferase immunoreactivity upon differentiation from said neuroepithelial stem cells.

5. The population of claim 1 wherein said CNS glial cells express glial fibrillary acid protein immunoreactivity upon differentiation from said neuroepithelial stem cells.

6. The population of claim 5 wherein said CNS glial cells express a ganglioside recognized by A2B5 antibody upon differentiation from said neuroepithelial stem cells.

7. The population of claim 1 wherein said glial CNS cells express a ganglioside recognized by A2B5 antibody upon differentiation from said neuroepithelial stem cells.

8. The population of claim 7 wherein said CNS glial cells express a sulfatide recognized by O4 antibody upon differentiation from said neuroepithelial stem cells.

9. The population of claim 7 wherein said CNS glial cells express galactocerebroside immunoreactivity upon differentiation from said neuroepithelial stem cells.

10. The population of claim 1 wherein said neuroepithelial stem cells are further capable of differentiation to glial-restricted precursor cells capable of self-renewal in adherent feeder-cell-independent culture medium and differentiation to CNS glial cells but not to CNS neuronal cells.

11. The population of claim 10 wherein said glial-restricted precursor cells express nestin and ganglioside immunoreactivities, but do not express glial fibrillary acidic protein, sulfatide, or galactocerebroside immunoreactivities upon differentiation from said neuroepithelial stem cells.

12. The population of claim 10 wherein said CNS glial cells express ganglioside and glial fibrillary acidic protein immunoreactivities upon differentiation from said glial-restricted precursor cells.

13. The population of claim 10 wherein said CNS glial cells express glial fibrillary acidic protein immunoreactivity but do not express ganglioside immunoreactivity upon differentiation from said glial-restricted precursor cells.

14. The population of claim 10 wherein said CNS glial cells express galactocerebroside immunoreactivity but do not express ganglioside immunoreactivity upon differentiation from said glial-restricted precursor cells.

15. An isolated, pure, homogeneous population of glial-restricted precursor cells derived from a neural tube from a rat embryo at a stage of development after closure of the neural tube, wherein said glial-restricted precursor cells self-renew in adherent feeder-cell-independent culture medium and differentiate into CNS glial cells, comprising oligodendrocytes, A2B5-positive astrocytes, and A2B5-negative astrocytes, but do not respond to PDGF by differentiating into CNS neuronal cells.

16. The population of claim 15 wherein said glial-restricted precursor cells express nestin immunoreactivity and a ganglioside recognized by A2B5 antibody but do not express glial fibrillary acidic protein immunoreactivity, sulfatide recognized by O4 antibody, or galactocerebroside recognized by GalC antibody.

17. The population of claim 15 wherein said CNS glial cells express a ganglioside recognized by A2B5 antibody and glial fibrillary acidic protein immunoreactivity upon differentiation from said glial-restricted precursor cells.

18. The population of claim 15 wherein said CNS glial cells express glial fibrillary acidic protein immunoreactivity but do not express a ganglioside recognized by A2B5 antibody upon differentiation from said glial-restricted precursor cells.

19. The population of claim 15 wherein said CNS glial cells express a galactocerebroside recognized by GalC antibody but do not express a ganglioside recognized by A2B5 antibody upon differentiation from said glial-restricted precursor cells.

* * * * *